(12) United States Patent
Douglas

(10) Patent No.: US 7,056,302 B2
(45) Date of Patent: Jun. 6, 2006

(54) INSERTION DEVICE FOR AN INSERTION SET AND METHOD OF USING THE SAME

(75) Inventor: Joel S. Douglas, Groton, CT (US)

(73) Assignee: Sterling Medivations, Inc., Norcross, GA (US)

( * ) Notice: Subject to any disclaimer, the term of this patent is extended or adjusted under 35 U.S.C. 154(b) by 0 days.

(21) Appl. No.: 10/505,514

(22) PCT Filed: Feb. 26, 2003

(86) PCT No.: PCT/US03/06219

§ 371 (c)(1),
(2), (4) Date: Feb. 22, 2005

(87) PCT Pub. No.: WO03/072164

PCT Pub. Date: Sep. 4, 2003

(65) Prior Publication Data

US 2005/0131346 A1    Jun. 16, 2005

Related U.S. Application Data

(60) Provisional application No. 60/359,649, filed on Feb. 26, 2002.

(51) Int. Cl.
A61M 5/20 (2006.01)

(52) U.S. Cl. ...................... 604/136; 604/117

(58) Field of Classification Search ................ 604/131, 604/136, 133, 137, 134, 138, 135, 200, 203, 604/204, 212, 244, 117
See application file for complete search history.

(56) References Cited

U.S. PATENT DOCUMENTS

| | | | | |
|---|---|---|---|---|
| 3,094,989 A | * | 6/1963 | Stauffer | 604/138 |
| 3,820,542 A | * | 6/1974 | Huschman | 604/196 |
| 4,227,528 A | * | 10/1980 | Wardlaw | 604/139 |
| 4,553,962 A | * | 11/1985 | Brunet | 604/198 |
| 4,886,499 A | * | 12/1989 | Cirelli et al. | 604/131 |
| 5,167,632 A | * | 12/1992 | Eid et al. | 604/136 |
| 6,517,517 B1 | * | 2/2003 | Farrugia et al. | 604/131 |
| 6,830,562 B1 | | 12/2004 | Mogensen et al. | |

* cited by examiner

Primary Examiner—Manuel Mendez
(74) Attorney, Agent, or Firm—Altera Law Group, LLC (57) ABSTRACT

A system for inserting at least a portion of an insertion set through the surface of a tissue, having: an inserter with a moveable plunger disposed within a cavity therein; an insertion set holder received into the distal end of the cavity; and an insertion set received into the insertion set holder, wherein the insertion set is moveable within the insertion set holder such that when the plunger is advanced into contact with the insertion set, the insertion set advances through the insertion set holder to a position at which at least a portion of the insertion set extends out of the distal end of the cavity.

18 Claims, 5 Drawing Sheets

INSERTION DEVICE FOR AN INSERTION SET AND METHOD OF USING THE SAME

This application claims priority to International Patent Application No. PCT/US03/06219, filed Feb. 26, 2003, entitled "Insertion Device for an Insertion Set and Method of Using the Same"; which claims priority to U.S. Provisional Application No. 60/359,649, filed Feb. 26, 2002, entitled "Insertion Device for an Insertion Set and Method of Using the Same".

TECHNICAL FIELD

The present invention is related to systems for placing various medical insertion sets (such as needles or infusion sets) into a patient's skin.

SUMMARY OF THE INVENTION

In various aspects, the present invention provides a system for inserting at least a portion of an insertion set through the surface of a tissue, comprising: an inserter with a moveable plunger disposed within a cavity therein; and an insertion set holder received into the distal end of the cavity; and an insertion set received into the insertion set holder, wherein the insertion set is moveable within the insertion set holder such that when the plunger is advanced into contact with the insertion set, the insertion set advances through the insertion set holder to a position at which at least a portion of the insertion set extends out of the distal end of the cavity.

In various aspects, the holder is held at a fixed position at the distal end of the of the cavity, but may easily be removed from the distal end of the cavity when the plunger has been advanced.

In other aspects of the invention, the present invention provides an inserter for inserting at least a portion of an insertion set through the surface of a tissue, comprising: a housing having a cavity therein, wherein the distal end of the cavity is adapted to receive a holder for an insertion set therein, the holder being adapted for slidable motion of the insertion set therein; and a moveable plunger disposed within the cavity for advancing the insertion set within the holder, wherein the plunger is moveable from a proximal position away from the insertion set to a distal position in contact with the insertion set.

In other aspects of the invention, the present invention provides an insertion set, comprising: a housing; a piercing member extending from the housing; and a holder, wherein the housing is slidably moveable within the holder from a first position at which a portion of the housing extends out of the holder and the piercing member does not extend out of the holder to a second position at which the piercing member extends out of the holder.

In various embodiments of the invention, the insertion set can be used with the present inserter, by itself, or with an adapter. Such adapter may include, but is not limited to, adapters as described in co-owned U.S. Provisional Patent Applications 60/407,531, filed Aug. 30, 2002 and 60/409, 119, filed Sep. 9, 2002.

In other aspects of the invention, the present invention provides a holder for an insertion set, the insertion set having a housing with a piercing member extending therefrom, the holder being dimensioned such that the housing is slidably moveable within the holder from a first position at which a portion of the housing extends out of the holder and the piercing member does not extend out of the holder to a second position at which the piercing member extends out of the holder.

In accordance with the present invention, a novel inserter is used to insert a piercing member of a novel insertion set into a patient. Together, the novel inserter and the novel insertion set are used in a novel system for inserting at least a portion of an the insertion set (e.g.: a piercing member of the insertion set) into a patient.

An advantage of the present invention is that it provides a simple, yet firm and stable system for inserting a needle or other piercing member(s) into a patient. In addition, the present invention provides a system for inserting a needle or other piercing member(s) into a patient at any angle to the patient's skin (i.e.: between 0 and 90 degrees).

According to an embodiment of the invention, an inserter is provided for quick and easy transcutaneous placement of a medical needle through the skin of a patient, particularly such as an insertion of a subcutaneous insertion set. The inserter is designed to place the needle through the skin at a selected insertion angle and with a controlled force and speed of insertion, to ensure proper needle placement with minimal patient discomfort. The inserter may preferably be designed to meet these objectives, while safeguarding against undesired projection of the medical needle through free space, in the event that the inserter is actuated in spaced relation to the patient's skin.

The inserter preferably comprises a spring-loaded plunger having a head for exerting force on a housing of an insertion set. The housing is designed for receiving and supporting the insertion set within an associated holder at a fixed location within the distal end of the inserter. When the plunger is advanced, it contacts the housing of the insertion set, and moves the housing of the insertion set (through the holder) to a position at which a needle (or other piercing member(s)) of the insertion set projects outwardly from the distal end of the inserter. Therefore, when the device is positioned against the patient's skin, and the plunger is advanced, the needle (or other piercing member(s)) of the insertion set projects through the patient's skin.

Thereafter, the inserter is removed, leaving behind the insertion set (and its associated holder) on the patient's skin. Thereafter, the holder is manually removed, leaving only the insertion set on the patient's skin, with the piercing member penetrating through the surface of the patient's skin.

In optional aspects, the plunger is designed for retraction and retention within a barrel to a cocked position with a drive spring compressed in a manner applying a predetermined spring force to the plunger head. A front or nose end of the inserter cavity or barrel is designed for attachment to the holder and the holder may be designed to be pressed placement against the skin of a patient, at a selected needle insertion site, and in an orientation with the needle disposed at a correct or desired insertion angle. A trigger member is operable to release the plunger and thereby permit the drive spring to carry the plunger toward the patient's skin with a controlled force and speed, thereby pushing the housing of the insertion set thereby resulting in proper transcutaneous placement of the insertion needle with minimal patient discomfort.

An advantage of the inserter design is that it does not require a return spring. (i.e.: a separate spring is not required for "arming" the inserter. Rather, the operator simply pulls the plunger upward to a retracted position prior to use.

The plunger head may optionally include a safety lock mechanism to retain the insertion set against projection from the inserter barrel. According to an embodiment, the safety lock mechanism comprises at least one safety lock arm(s) for engaging and retaining the insertion set when the plunger is retracted from a fully advanced position. Each safety lock arm may optionally include a cam lobe for engaging an appropriately shaped recess on the insertion set to prevent release thereof from the plunger head, unless and until the plunger head is returned to the fully advanced position. In such fully advanced position, the shape of the cam lobe may permit quick and easy separation of the inserter from the insertion set with a minimal separation force.

In operation, the safety lock arms thus prevent projection of the housing and the insertion set from the inserter, in the event that the trigger member is actuated with the nose end of the barrel of the inserter spaced from the skin of a patient. In that event, the plunger head is advanced with the controlled force and speed to the fully advanced position, but the insertion set is not thrown from the inserter as a projectile. Instead, the housing of the insertion set travels rapidly when impacted by the plunger head moving from a retracted position to a fully advanced position.

In other optional embodiments, the safety lock mechanism comprises a plunger head having a cylindrical shape defining a forwardly open cavity for receiving and supporting an insertion set (and its associated holder) with the insertion needle projecting outwardly. In this embodiment, the plunger head may include a radially inwardly projecting rim at a forward or nose end thereof, wherein the rim defines an oval-shaped opening. The size of the rim opening may permit relatively free reception of a hub on the insertion set, with the insertion set oriented at an angle relative to a central axis of the plunger head and barrel. The insertion set may then be reoriented to align the insertion needle coaxially with the central axis of the barrel and plunger head while being captivated in the body of the holder, so that the holder is received into a recess and is retained against undesired release from the inserter during spring-driven placement of the needle. After needle placement, the inserter may be released from the insertion set with minimal separation force by orienting the inserter angularly relative to the insertion set to permit free slide out passage of the hub through the oval rim opening.

In other optional embodiments of the present invention, the insertion set holder also includes a receiving structure to support the insertion set in a position with the at least one piercing member oriented for insertion through the skin of the patient at a predetermined angle relative to the skin of the patient upon movement of the plunger from the retracted position to the advanced position. As will be explained, this holder is manually separable from the housing of the insertion set. The plunger or other suitable driver is operatively coupled to the housing and the housing is oriented such that the plunger will urge the housing of the insertion set with a controlled force and speed from the retracted position toward the advanced position to place at least a portion of the at least one piercing member of the insertion set thorough the skin of the patient to install the insertion set to the patient. The insertion set holder is removable from the insertion set while maintaining the installation of the insertion set to the patient.

In particular embodiments, the predetermined angle relative to the skin is about 90 degrees, between 90 degrees and 10 degrees, or is after insertion between 0 and 10 degrees. In additional embodiments, the insertion set is a transuctaneous insertion set, a subcutaneous insertion set, an infusion set, sensor set or the like. In still other embodiments, the insertion set rests mainly on the surface of the skin after insertion or the insertion set is implanted in the skin of the patient. According to the invention's embodiments, the at least one piercing member is a needle. In alternative embodiments, the at least one piercing member is a plurality of needles, and can also be a plurality of micro-needles. Also, in some embodiments, the insertion set insertion set can be both an infusion set and a sensor set combined into an integral unit.

In yet other optional embodiments, the insertion set holder has a forward end defining a generally planar angled insertion contact surface for placement against the skin of a patient with the holder in a predetermined orientation relative to the patient's skin that mirrors the predetermined angle relative to the skin of the patient. Other embodiments include a trigger mechanism that actuates the driver. For instance, the trigger mechanism includes at least one trigger for fingertip depression to actuate the driver for movement of the insertion set housing (through the insertion set holder) from the retracted position to the advanced position. In addition, the plunger/driver can include at least one spring for spring-loaded movement of the plunger head used to urge the plunger body from the retracted position to the advanced position. Further, the plunger/driver can include a force changing mechanism that permits alteration of the controlled force and speed of the insertion set housing moving from the retracted position to the advanced position. In still further embodiments, the insertion set housing and its associated holder include a cooperatively engageable track mechanism for guiding movement of the housing between the advanced and retracted positions while retaining the housing against rotation relative to the inserter holder.

In additional optional embodiments of the insertion set, the at least one piercing member is provided with a piercing member hub. In addition, the receiving structure of the insertion set holder may include a recess formed therein for mated slide-fit reception of the piercing member hub of the insertion set. Further, the recess of the receiving structure can include a laterally open undercut recess. Alternatively, the receiving structure may include a safety retainer structure that retains the at least one piercing member on the receiving structure during movement from the retracted position to the advanced position. This safety retainer structure permits separation of the at least one piercing member from the plunger body when the plunger body is in the advanced position.

In optional embodiments of the insertion set, the set housing is coupled to the at least one piercing member. Also, the set housing is shaped to fit within the holder to orient the at least one piercing member for placement through the skin of the patient of at least a portion of the at least one piercing member at a predetermined angle relative to the skin of the patient to install the insertion set to the patient. The set housing of the insertion set is removable from the receiving structure of the inserter while maintaining the installation of the insertion set to the patient.

In particular embodiments of the insertion set, the predetermined angle relative to the skin is about 90 degrees, between 90 degrees and 10 degrees, or is after insertion between 0 and 10 degrees. In additional embodiments, the insertion set is a transuctaneous insertion set, a subcutaneous insertion set, an infusion set, sensor set or the like. In still other embodiments, the insertion set rests mainly on the surface of the skin after insertion or the insertion set is implanted in the skin of the patient. According to various embodiments, the at least one piercing member is a needle. In alternative embodiments, the at least one piercing member is a plurality of needles, and can also be a plurality of micro-needles. Also, in some embodiments, the insertion set can be both an infusion set and a sensor set combined into an integral unit.

Other features and advantages of the invention will become apparent from the following detailed description, taken in conjunction with the accompanying drawings which illustrate, by way of example, various features of embodiments of the invention.

DETAILED DESCRIPTION OF THE INVENTION

The present invention may be understood more readily by reference to the following detailed description of the various embodiments of the invention and the Figures.

Before the present articles and methods are disclosed and described, it is to be understood that the terminology used herein is for the purpose of describing particular embodiments only and is not intended to be limiting. It must be noted that, as used in the specification and the appended claims, the singular forms "a", "an" and "the" include plural referents unless the context clearly dictates otherwise.

As shown in the drawings for purposes of illustration, the invention is embodied in a system comprising an inserter, an insertion set holder and an insertion set. In various embodiments, the insertion sets may comprise any form of infusion set, sensor set, medical device, or the like. Further embodiments of the present invention may be used to insert other insertion sets or medical devices such as biodegradable implants, capsules, impregnated threads (with medications or the like). Other insertion sets may be directed to a threaded needle insertion set, such as that described in U.S. Pat. No. 5,584,813 issued Dec. 17, 1996 to Livingston et al. entitled "Subcutaneous Injection Set" and U.S. Pat. No. 5,779,665 issued on Jul. 14, 1998 to Mastrototaro et al. entitled "Transdermnal Introducer Assembly", which are herein incorporated by reference. In addition, the insertion sets may be coated with medications, or other agents, that inhibit infection and/or promote healing of the insertion site. Various embodiments of the invention include insertion sets for transcutaneous placement in subcutaneous tissue. However, according to various embodiments, the insertion set may be inserted into other subdermal tissues. In addition, still further embodiments may be used to place the sets in other types tissue, such as muscle, lymph, organ tissue or the like, and used in animal tissue.

According to the embodiments of the present invention, the inserter and insertion set holder is loaded with a standard hand-held insertion set, or the like, and then placed against the skin of the user, where the insertion device and plunger is activated to transcutaneously place a portion of the insertion set, or the like, subcutaneously in a quick manner that minimizes pain and/or discomfort to the user. However, it will be recognized that further embodiments of the invention may be used to place an entire insertion set, or the like, beneath the skin, rather than just a portion of the insertion set. As discussed, embodiments of the insertion device and plunger are designed to accommodate off-the-shelf insertion sets, or the like. But, alternative embodiments may be used with customized insertion sets, or the like that have been altered to fit the insertion device and plunger in a particular orientation or configuration to improve safety and/or assure proper placement of the insertion set, or the like. In still other embodiments, the insertion sets, or the like may be angled and the devices are capable of insertion at angles between 0 and 90 degrees relative to the skin surface after insertion of the insertion set.

According to embodiments of the present invention, the insertion set includes at least one piercing member to pierce the skin during insertion. In particular embodiments, the piercing member is a metal needle. In alternative embodiments, the needle may be hollow, solid, half needle (or other fraction), or the like. In further alternative embodiments, the piercing member may be made out of other materials, such as ceramic, plastic, composites, silicon micro-needles, biodegradable, hydrophilic substances, substances that soften and/or change once in contact with the body and/or bodily fluids, or the like. In other alternative embodiments, the insertion set may include more than one piercing member. For example, a single insertion set may include a piercing member for an infusion portion and another piercing member for a separate sensor portion, or the like. Alternatively, the insertion set may include a plurality of small piercing members on a small patch or substrate, such as a series of hollow micro-needles (such as from silicon, plastics, metal or the like) for infusion of a medication or a series of solid micro-needles for sensor applications (such as from silicon, plastics, metal or the like), which micro-needles are used to penetrate the skin.

As shown in the exemplary drawings, an inserter in accordance with a first embodiment of the present invention is referred to generally by the reference numeral 10 is provided for quick and easy transcutaneous placement of a medical needle, particularly such as an insertion needle 12 of the type provided with a subcutaneous insertion set 14 as depicted in FIGS. 2A to 2D. The inserter 10 may include a trigger-type actuator mechanism for transcutaneous placement of the insertion needle 12 with a controlled speed and force, and with the insertion needle 12 oriented at a desired angular position relative to the skin 16 of the patient.

Inserter 10 of the present invention, as shown in the illustrative drawings, is particularly designed for placement of the insertion needle 12 of a subcutaneous insertion set 14, such as an insertion set of the general type shown and described in U.S. Pat. Nos. 4,755,173; 5,176,662; and 5,257,980, which are incorporated by reference herein. Such insertion sets 14 are used to infuse medical fluids such as selected medications to a patient, with one example being the administration of insulin to a diabetic by operation of a programmable medication infusion pump (not shown) of the type described in U.S. Pat. No. 4,685,903. Alternatively, the inserter 10 may be used to transcutaneously place a medical needle associated with other types of insertion sets, such as transcutaneous sensor insertion sets of the general type shown and described in U.S. Pat. Nos. 5,390,671; 5,560,806 and 5,586,553, which are also incorporated by reference herein. Such insertion sets are used, for example, to monitoring patient glucose levels.

Figure 1A:
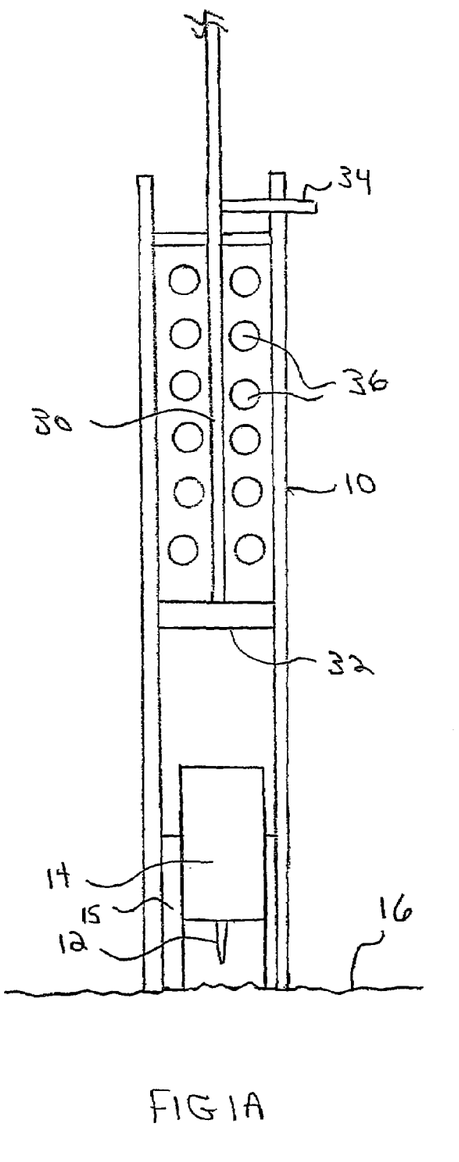
FIG. 1A shows a sectional side elevation view of an inserter with an insertion set received in its distal end prior to positioning the insertion set in a patient.

FIG. 1A shows inserter 10 supporting an insertion set holder 15 within its distal end. An insertion set 14 is slidably received within holder 15. Inserter 10 has a hollow cavity in which plunger 30 is disposed. When plunger 30 is moved from the position in FIG. 1A to the position in FIG. 1B, plunger head 32 pushes against body 14 of insertion set 20, thereby moving body 14 such that needle 12 penetrates the patient's skin 16.

Figure 2A:
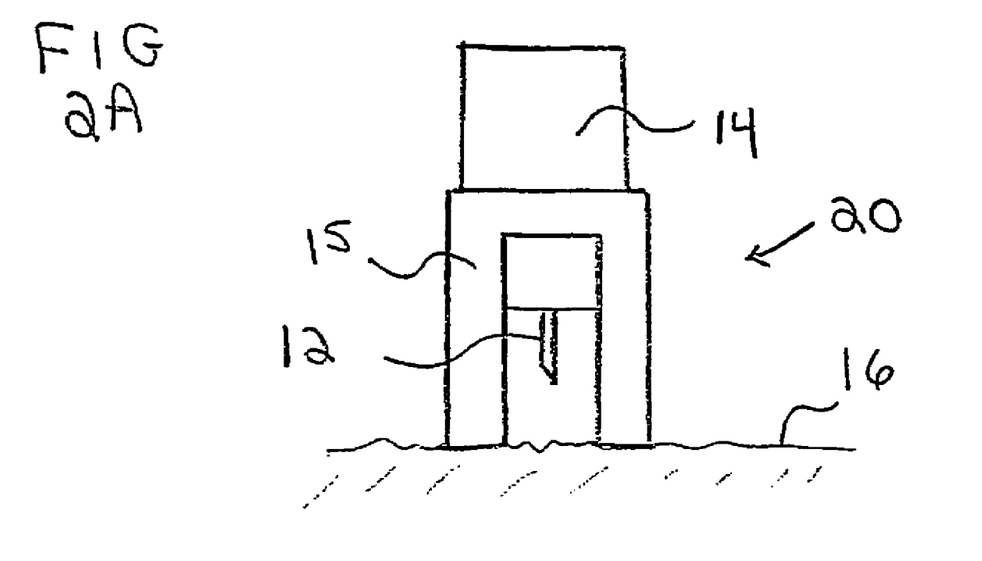
FIG. 2A is a side elevation view of the insertion set and its associated holder prior to needle deployment.
Figure 2B:
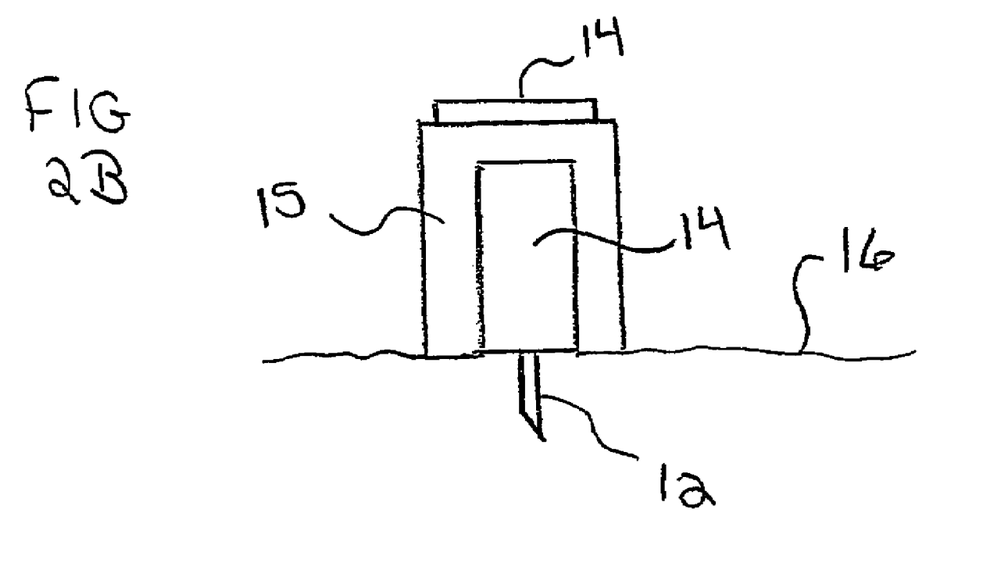
FIG. 2B is a side elevation view of the insertion set and its associated holder after needle deployment.
Figure 2C:
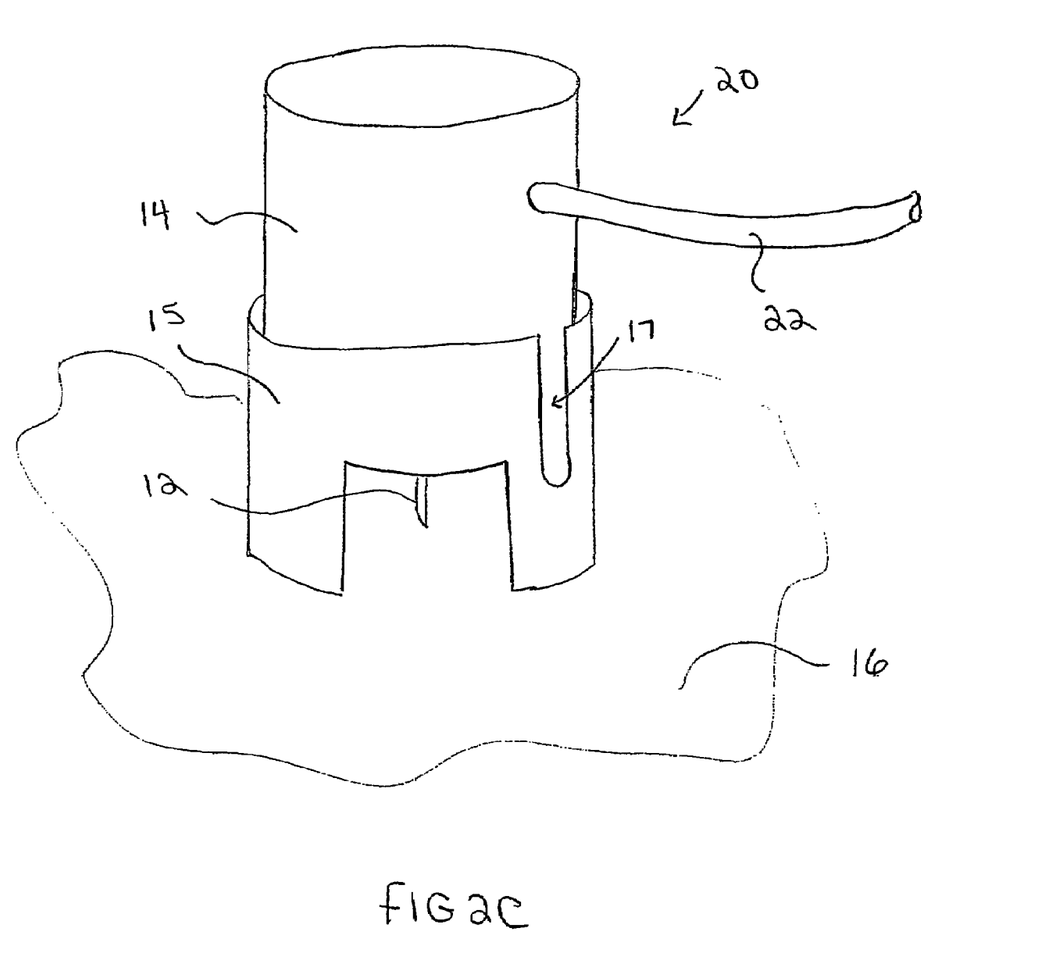
FIG. 2C is a perspective view corresponding to FIG. 2A.
Figure 2D:
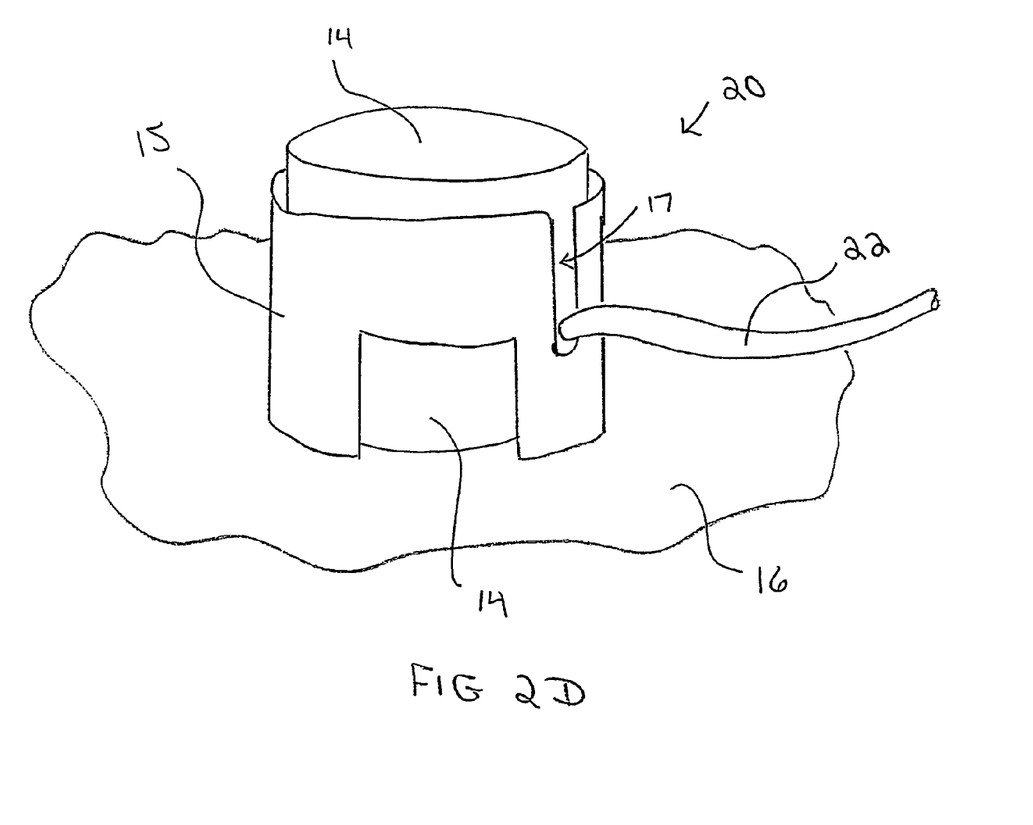
FIG. 2D is a perspective view corresponding to FIG. 2B.
Figure 3A:
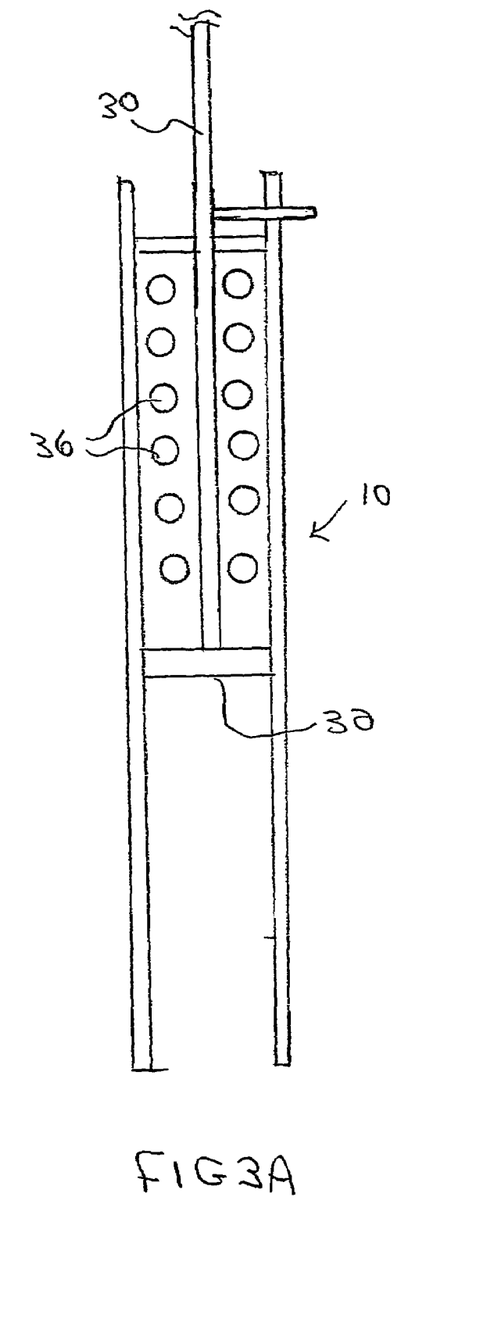
FIG. 3A shows the inserter prior to deployment.
Figure 3B:
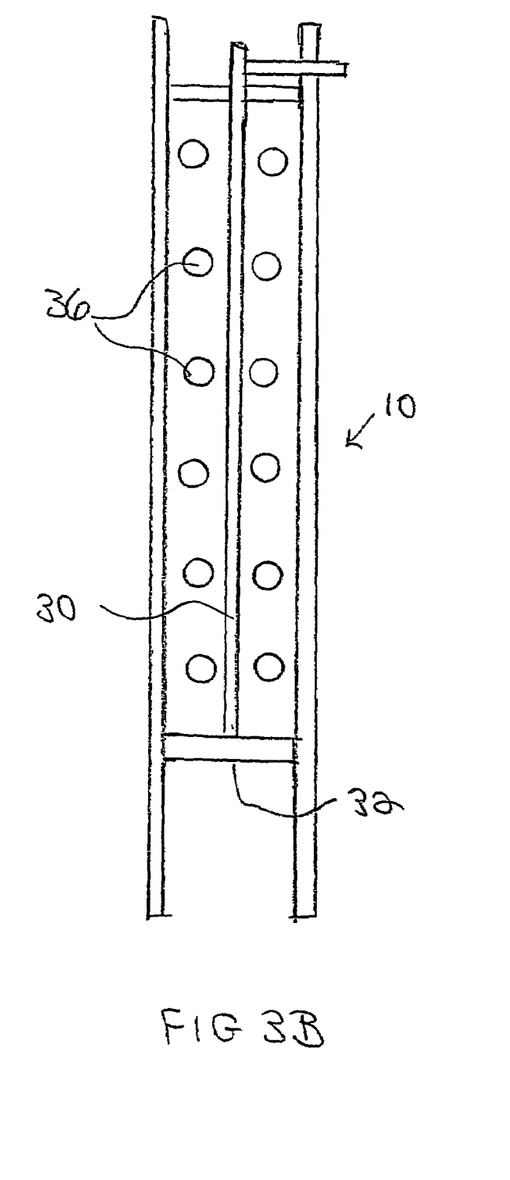
FIG. 3B shows the inserter after its deployment.

In accordance with the present invention, body 14 of insertion set 20 is slidably moveable within insertion set holder 15. Holder 15 can be manually separated from housing 14. This is seen most clearly in FIGS. 2A to 2D where the insertion set 20 (including housing 14, needle 12 and holder 15) is initially positioned as shown in FIGS. 2A and 2C when received into the distal end of the cavity or barrel of inserter 10. After plunger 30 has been advanced, plunger head 32 will advance body 14 through holder 15 such that needle 12 penetrates the patient's skin 16.

In further optional aspects of the invention, insertion set 20 may include infusion tubing 22 to permit medication delivery (through needle 12) into the patient. As can also be seen in FIGS. 2C and 2D, holder 15 may include a slot 17 in which tubing 22 is free to travel. Body 14 may further comprise an internal chamber (not shown) for receiving medication via infusion tubing 22. Body 14 of insertion set 20 may further comprise a large winged base (not shown) through which needle 12 extends. The bottom surface of the winged base may have an adhesive covering (with a peel-away covering) to assist in affixing body 14 to the patient's skin.

The inserter 10 of the present invention represents a simple device which can be used by the patient to quickly and easily place the subcutaneous insertion set 20 in a proper transcutaneous position and orientation, at a selected medication insertion site. The inserter 10 is preferably designed to project the insertion set toward the patient's skin 16 at a controlled force and speed for quickly piercing the skin in a manner insuring proper placement of the insertion needle 12, while minimizing patient anxiety and/or discomfort. Improper and/or partial placement of the insertion needle 12 is thus avoided.

Figure 1B:
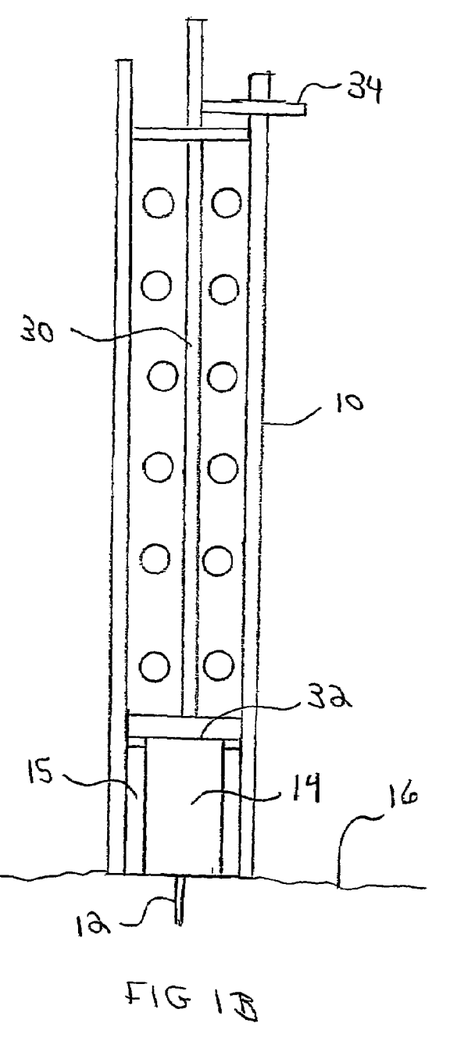
FIG. 1B shows the system of FIG. 1A after a plunger has been advanced in the inserter, thereby sliding the insertion set through its associated housing such that a piercing needle of the insertion set has been deployed into a patient.

As shown in FIG. 1A and 1B, holder 15 is received into the distal end of inserter 10. Holder 15 preferably remains in the same position in inserter 10 as housing 14 (and needle 12) are advanced by plunger 30. After the present invention has been deployed, inserter 10 is then removed, leaving holder 15 and insertion set body 14 sitting on the patient's skin. Thereafter, the patient simply pulls holder 15 away from insertion set body 14. Thus, after deployment, insertion set body 14 remains sitting on the patient's skin (with associated needle 12 penetrating into the patient's skin).

The plunger 30 of inserter 10 is preferably driven downward by springs 36 (shown in sectional view). A trigger 34 may be used to release spring 36 so that plunger 30 moves downward from the position of FIGS. 1A/3A to that of 1B/3B.

Preferably, trigger 34 (or other suitable driver actuator such as air, spring or solenoid valve) is adapted to hold the plunger 30 in a retracted position, against the force of a compressed drive spring 36. Fingertip depression of trigger 34 releases plunger 30 for spring-loaded travel toward the advanced position.

In optional aspects, the body 14 and holder 15 of insertion set 20 are designed such that the system is biased to move to the position shown in FIGS. 2A/2C. This is particularly advantageous in avoiding needle contact when the operator is loading insertion set 20 into the distal end of the barrel of inserter 10. In this aspect of the invention, the downward force of plunger 30 (when spring 36 is released by trigger 34) will overcome the internal biasing of insertion set 20, instead moving it to the deployed position shown in FIGS. 2B and 2D.

The foregoing embodiments and advantages are merely exemplary and are not to be construed as limiting the present invention. The present teaching can be readily applied to other types of devices and applications that may be common to those of ordinary skill in the art. The description of the present invention is intended to be illustrative, and not to limit the scope of the claims. Many alternatives, modifications, and variations will be apparent to those skilled in the art.

What is claimed is:

1. A transcutaneous infusion inserter for inserting at least a portion of an transcutaneous insertion set onto the surface of the tissue surface inserting an insertion needle through the surface of a tissue, comprising: a housing having a cavity therein, wherein the distal end of the cavity is adapted to receive a removable holder for an insertion set therein, the holder being adapted for slidable motion of the insertion set therein; and a moveable plunger disposed within the cavity for advancing the insertion set within the holder, wherein the plunger is moveable from a proximal position away from the insertion set to a distal position in contact with the insertion set, said insertion set being releasable and separable from said inserter once said plunger has applied the insertion set to the surface of the tissue.

2. The inserter of claim 1, wherein the holder is slideably removable from the distal end of the cavity.

3. The inserter of claim 1, wherein the distal end of the cavity is adapted to receive the holder in a fixed position thereat.

4. A system for applying an insertion set to the surface of a tissue and for inserting at least a portion of an insertion set through the surface of a tissue, comprising: an inserter with a moveable plunger disposed within a cavity therein; and an insertion set holder slideably and removeably received into the distal end of the cavity; and an insertion set received into the insertion set holder, wherein the insertion set is moveable within the insertion set holder such that when the plunger is advanced into contact with the insertion set, the insertion set advances through the insertion set holder to a position at which at least a portion of the insertion set extends out of the distal end of the cavity, and wherein said insertion set is separable from said inserter after application from the tissue.

5. The device of claim 4, wherein the insertion set includes a contact surface for contacting the tissue and said surface includes means for adhering to the surface.

6. The system of claim 4, wherein the insertion set includes a contact surface for contacting the tissue and said surface includes an adherent for attaching to said surface and drawing said set out of said inserter.

7. The device of claim 4, wherein the insertion set is releaseably held at a fixed position in the distal end of the cavity.

8. The system of claim 4, wherein the insertion set is includes a holder which substantially surrounds said set and is sized to be slideably received within said inserter and wherein said infusion set is slideable within said holder, that when said plunger engages said infusion set, it is slide within said holder into contact with the tissue and then said holder is slideably removable from the inserter.

9. An insertion set for simultaneously contact and piercing living tissue, comprising: a housing; a piercing member extending from the housing; and a holder, wherein the housing is slideably moveable within the holder from a first position at which a portion of the housing extends out of the holder and the piercing member does not extend out of the holder to a second position at which the piercing member extends out of the holder and wherein said housing is removable from said holder to allow said housing to remain in contact with said tissue after separation from said holder.

10. The system of claim 9, wherein the insertion set further comprises: infusion tubing extending from the housing for infusing or extraction of tissue fluids.

11. The insertion set of claim 9, wherein the housing holds the insertion set such that the piercing member of the insertion set is at an angle of between 10 and 90 degrees to the skin.

12. An inserter system for inserting at least a portion of a combination insertion and sensor set capable of infusing fluid into tissue and sensing tissue fluids, onto the surface of the tissue surface by inserting at least one insertion needle through the surface of a tissue, comprising: an inserter having a housing and a cavity therein, wherein the distal end of the cavity is adapted to receive an insertion and sensor set therein, the holder being adapted for slidable motion of the insertion set therein; and a moveable plunger disposed within the cavity for advancing the insertion and sensor set, wherein the plunger is moveable from a proximal position away from the insertion and sensor set to a distal position in contact with the insertion and sensor set, said set being releasable and separable from said inserter once said plunger has applied the set to the surface of the tissue.

13. The system of claim 12 wherein said insertion and sensor set includes at least one piercing member associated for infusing of fluids and at least one piercing member associated with the sensor sensing of bodily fluids.

14. The system of claim 13 wherein said at least one piercing member of the set are space apart from each other, so that fluid infused is not immediately sensed by said piercing member associated with said sensor set.

15. The system of claim 12 wherein said insertion and sensor set comprises a substrate including a plurality of needles.

16. The system of claim 15 wherein said needles are micro-needles.

17. The system of claim 12 wherein said piercing members of a biodegradable material.

18. The system of claim 12 wherein said piercing members are constructed to soften after insertion into tissue.

* * * * *